United States Patent [19]
Edwards et al.

[11] Patent Number: 5,484,400
[45] Date of Patent: Jan. 16, 1996

[54] DUAL CHANNEL RF DELIVERY SYSTEM

[75] Inventors: Stuart D. Edwards, Los Altos; Hugh R. Sharkey, Redwood City; Ingemar H. Lundquist, Pebble Beach; Ronald G. Lax, Grass Valley; Bruno Strul, Palo Alto; Roger A. Stern, Cupertino, all of Calif.

[73] Assignee: Vidamed, Inc., Menlo Park, Calif.

[21] Appl. No.: 216,315

[22] Filed: Mar. 23, 1994

Related U.S. Application Data

[63] Continuation-in-part of Ser. No. 929,638, Aug. 12, 1992, abandoned, and a continuation-in-part of Ser. No. 12,370, Feb. 2, 1993, Pat. No. 5,370,675, and a continuation-in-part of Ser. No. 61,072, May 14, 1993, Pat. No. 5,385,544.

[51] Int. Cl.⁶ .................................................. A61B 17/39
[52] U.S. Cl. ................................................................ 604/22
[58] Field of Search ............................. 604/19–22, 53, 604/164, 280; 606/39, 45, 32; 601/2; 607/96, 101, 102, 113, 115, 116, 138, 156

[56] References Cited

U.S. PATENT DOCUMENTS

| | | |
|---|---|---|
| 4,311,154 | 1/1982 | Sterzer et al. . |
| 4,312,364 | 1/1982 | Convert et al. . |
| 4,397,314 | 8/1983 | Vaguine . |
| 4,448,198 | 1/1984 | Turner . |
| 4,669,475 | 6/1987 | Turner . |
| 4,676,258 | 6/1987 | Inokuchi et al. . |
| 4,785,829 | 11/1988 | Convert et al. . |
| 4,907,589 | 3/1990 | Cosman . |
| 5,122,137 | 6/1992 | Lennox . |
| 5,197,466 | 3/1993 | Marchosky et al. . |
| 5,220,927 | 6/1993 | Astrahan et al. . |
| 5,249,585 | 10/1993 | Turner et al. . |

Primary Examiner—C. Fred Rosenbaum
Assistant Examiner—Manuel Mendez
Attorney, Agent, or Firm—Flehr, Hohbach, Test, Albritton & Herbert

[57] ABSTRACT

A method and an apparatus for delivering controlled heat independently on separate channels to perform ablation to treat benign prosthetic hypertrophy or hyperplasia (BPH). The dual channel power system provides independent control of radio frequency energy to each of two stylets protruding from a catheter into a human prostate through the urethra. The energy is independently transferred directly into the respective tissue around the stylets in such a manner as to provide respective tissue ablation without damage to surrounding tissues. Automatic shut-off of both channels occurs when any one of a number of surrounding areas to include the urethra or surrounding mass or the adjacent organs exceeds predetermined safe temperature limits. Automatic shut off of the individual channels occurs when the temperature of the tissue proximal to the respective stylet exceeds respective predetermined values. The dual channel system is microprocessor controlled and contains self-test startup and thermocouple autocalibration circuitry.

9 Claims, 7 Drawing Sheets

DUAL CHANNEL RF DELIVERY SYSTEM

This application is a Continuation-in-Part of application Ser. No. 07/929,638 filed Aug. 12, 1992 now abandoned and application Ser. No. 08/012,370 Filed on Feb. 2, 1993 and now U.S. Pat. No. 5,370,675 and Ser. No. 08/061,072 filed on May 14, 1993 now U.S. Pat. No. 5,385,544, the entire contents of which are hereby incorporated by reference.

BACKGROUND OF THE INVENTION

1. Field of the Invention

This invention is directed to a unique method and device for delivering controlled heat to perform ablation to treat benign prosthetic hypertrophy or hyperplasia (BPH). The method and the apparatus deliver this controlled heat into tissue penetrated by devices such as those disclosed in the copending above-referenced applications.

2. Discussion of Background

Treatment of cellular tissues usually requires direct contact of target tissue with a medical instrument, usually by surgical procedures exposing both the target and intervening tissue to substantial trauma. Often, precise placement of a treatment probe is difficult because of the location of a target tissue in the body or the proximity of the target tissue to easily damaged, critical body organs, nerves, or other components.

Benign prostatic hypertrophy or hyperplasia (BPH), for example, is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and dribbling. The association of BPH with aging has been shown to exceed 50% in men over 50 years of age and increases in incidence to over 75% in men over 80 years of age. Symptoms of urinary obstruction occur most frequently between the ages of 65 and 70 when approximately 65% of men in this age group have prostatic enlargement.

Currently there is no proven effective nonsurgical method of treatment of BPH. In addition, the surgical procedures available are not totally satisfactory. Currently patients suffering from the obstructive symptoms of this disease are provided with few options: continue to cope with the symptoms (i.e., conservative management), submit to drug therapy at early stages, or submit to surgical intervention. More than 30,000 patients per year undergo surgery for removal of prostatic tissue in the United States. These represent less than five percent of men exhibiting clinically significant symptoms.

Those suffering from BPH are often elderly men, many with additional health problems which increase the risk of surgical procedures. Surgical procedures for the removal of prostatic tissue are associated with a number of hazards including anesthesia associated morbidity, hemorrhage, coagulopathies, pulmonary emboli and electrolyte imbalances. These procedures can also lead to cardiac complications, bladder perforation, incontinence, infection, urethral or bladder neck stricture, retention of prostatic chips, retrograde ejaculation, and infertility. Due to the extensive invasive nature of the current treatment options for obstructive uropathy, the majority of patients delay definitive treatment of their condition. This circumstance can lead to serious damage to structures secondary to the obstructive lesion in the prostate (bladder hypertrophy, hydronephrosis, dilation of the kidney pelves, etc.) which is not without significant consequences. In addition, a significant number of patients with symptoms sufficiently severe to warrant surgical intervention are poor operative risks and are poor candidates for prostatectomy. In addition, younger men suffering from BPH who do not desire to risk complications such as infertility are often forced to avoid surgical intervention. Thus the need, importance and value of improved surgical and non-surgical methods for treating BPH is unquestionable.

High-frequency currents are used in electrocautery procedures for cutting human tissue, especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy which is rapidly dissipated and reduced to a non-destructive level by conduction and convection forces of circulating fluids and other natural body processes.

Microwave, radiofrequency, acoustical (ultrasound) and high energy (laser) devices, and tissue destructive substances have been used to destroy malignant, benign and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave antenna through a duct to the zone of treatment and apply energy diffusely through the duct wall into the surrounding tissue in all directions. Severe trauma is often sustained by the duct wall during this cellular destruction process, and some devices combine cooling systems with microwave antennas to reduce trauma to the ductal wall. For treating the prostate with these devices, for example, heat energy is delivered through the walls of the urethra into the surrounding prostate cells in an effort to kill the tissue constricting the urethra. Light energy, typically from a laser, is delivered to prostate tissue target sites by "burning through" the wall of the urethra. Healthy cells of the duct wall and healthy tissue between the nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

Application of liquids to specific tissues for medical purposes is limited by the ability to obtain delivery without traumatizing intervening tissue and to effect a delivery limited to the specific target tissue. Localized chemotherapy, drug infusions, collagen injections, or injections of agents which are then activated by light, heat or chemicals would be greatly facilitated by a device which could conveniently and precisely place a fluid supply catheter opening at the specific target tissue.

SUMMARY OF THE INVENTION

It is an object of the present invention to provide an RF generation system having individual delivery of power to each of two channels wherein the power level and the duration of the applied power is individually controllable for the selective application of heat to perform ablation in a number of various modes. Therefore two needles can operate independently and simultaneously either at the same power and same temperature or one at a higher power than the other.

It is a further object of the present invention to provide a power supply source which automatically compensates for differences in deployment length of electrodes or deployment length of shields covering those electrodes.

It is a further object of the present invention to provide an RF power delivery system which has the ability to provide self-testing by having each independent generator connected to an internal test load.

It is a further object of the present invention to provide calibration of thermocouple amplifier circuitry by incorporating a precision reference voltage source and switching this source into the amplifier circuitry for calibration.

These and other objects of the present invention are accomplished by a dual channel RF generator source with programmable output power which corresponds to a set point on the front panel of the device wherein the system also contains an autocalibration of thermocouple amplifier circuitry that and a self-test system which uses an internal test load so that each channel can be tested and so that the thermocouple circuit can be tested. A precision reference voltage source allows for the conversion of any thermocouple voltage into a temperature without requiring an offset or scale factor adjustment.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
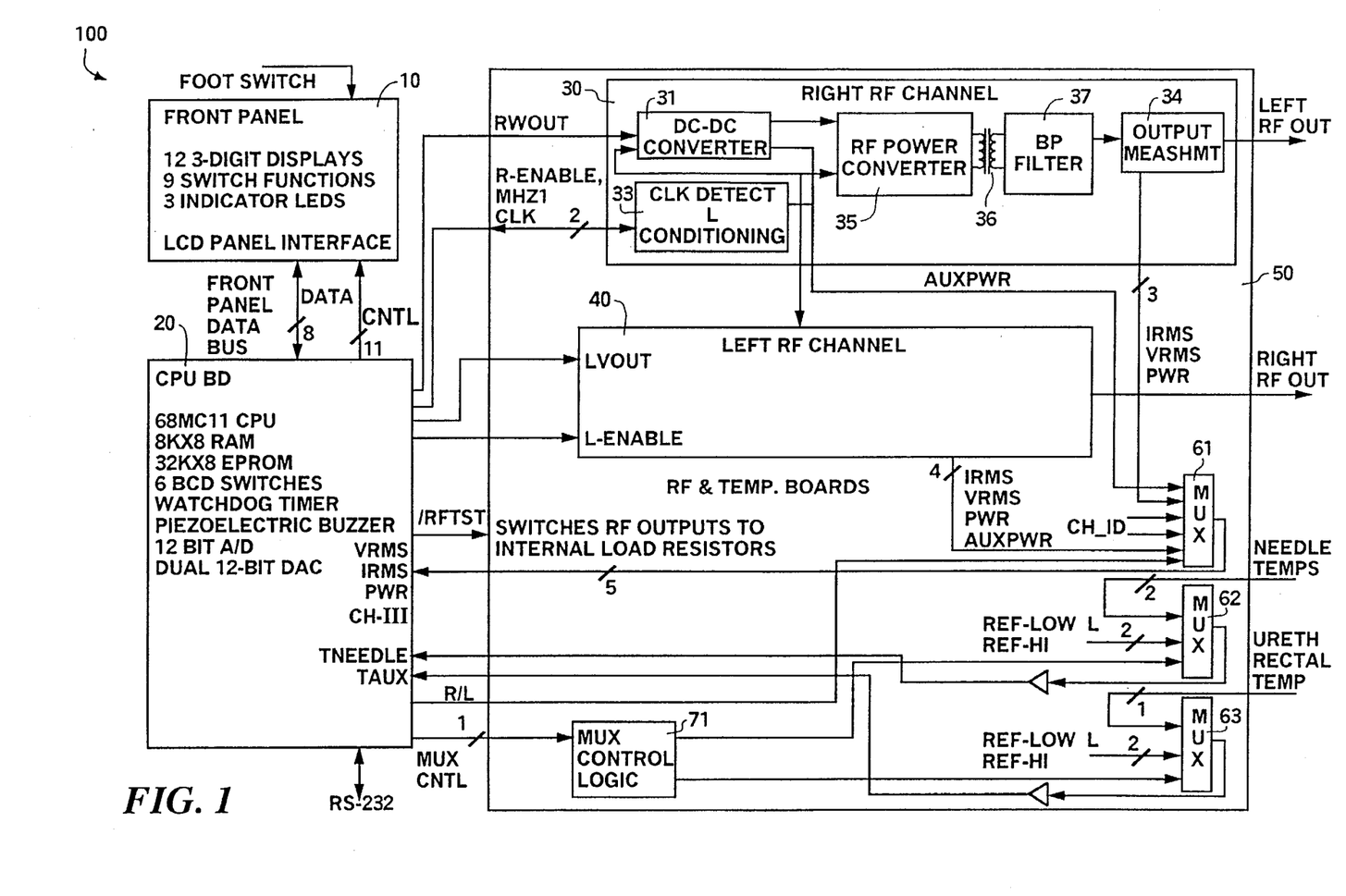
FIG. 1 is block diagram of the RF delivery system of the present invention.

Referring now to the drawings, wherein like reference numerals designate identical or corresponding parts throughout the several views, and more particularly to FIG. 1 thereof, an RF dual channel delivery system is shown in block diagram form. Radio frequency RF energy is generated by an RF/Temperature board 50 which generates variable output voltages used to produce tissue heating. The dual channel output is represented by right and left channels 30 and 40 with each channel containing a DC-DC converter 31 and a clock detector and conditioning circuit 33 both of which are controlled by a CPU 20. An RF power converter 35 along with a transformer 36 and a band pass filter 37 provide power which is measured at circuit 39 to be fed out to the appropriate output for a needle and the power output measurement is also fed to a multiplexer 61 wherein the output of the multiplexer 61 is fed to the CPU 20. The same circuitry associated with right channel exists 30 in the left channel 40 whose measured output is also fed to multiplexer 61. Multiplexers 62 and 63 provide temperature feedback from the needles and the other temperature measurements such as urethral or rectal probes. Control of the multiplexers 62 and 63 is provided by logic 71 in order to provide the required safety turnoff when the temperature exceeds a predetermined value. The CPU 20 provides data flow and control of a front panel 10 as well as provides a switching of RF outputs to internal load resistors of the RF/temperature boards. These load resistors inside the RF board can be switched into the circuit and placed at the RF outputs so that the output circuitry can consequently be automatically tested during the power-up sequence under realistic operating conditions. The CPU, in the preferred embodiment, utilizes a Motorola 68HC11 control processor having 8K×8 bits of RAM and 32K×8 bits of EPROM. Six configuration switches each allows selection of one of sixteen different configuration options and the board includes an RS-232 interface configured as data terminal equipment. Input ports read the front panel switches and a foot switch. A 12 bit A/D converter is used with multiplexed input to read thermocouple and RF power measurement data with a dual 12-bit digital-to-analog converter for RF output voltage control. A watchdog timer inhibits RF signal generation during hardware or software failure and a piezoelectric buzzer is used for a tone to indicate RF power being active and to provide audio feedback for front panel key presses.

Figure 2:
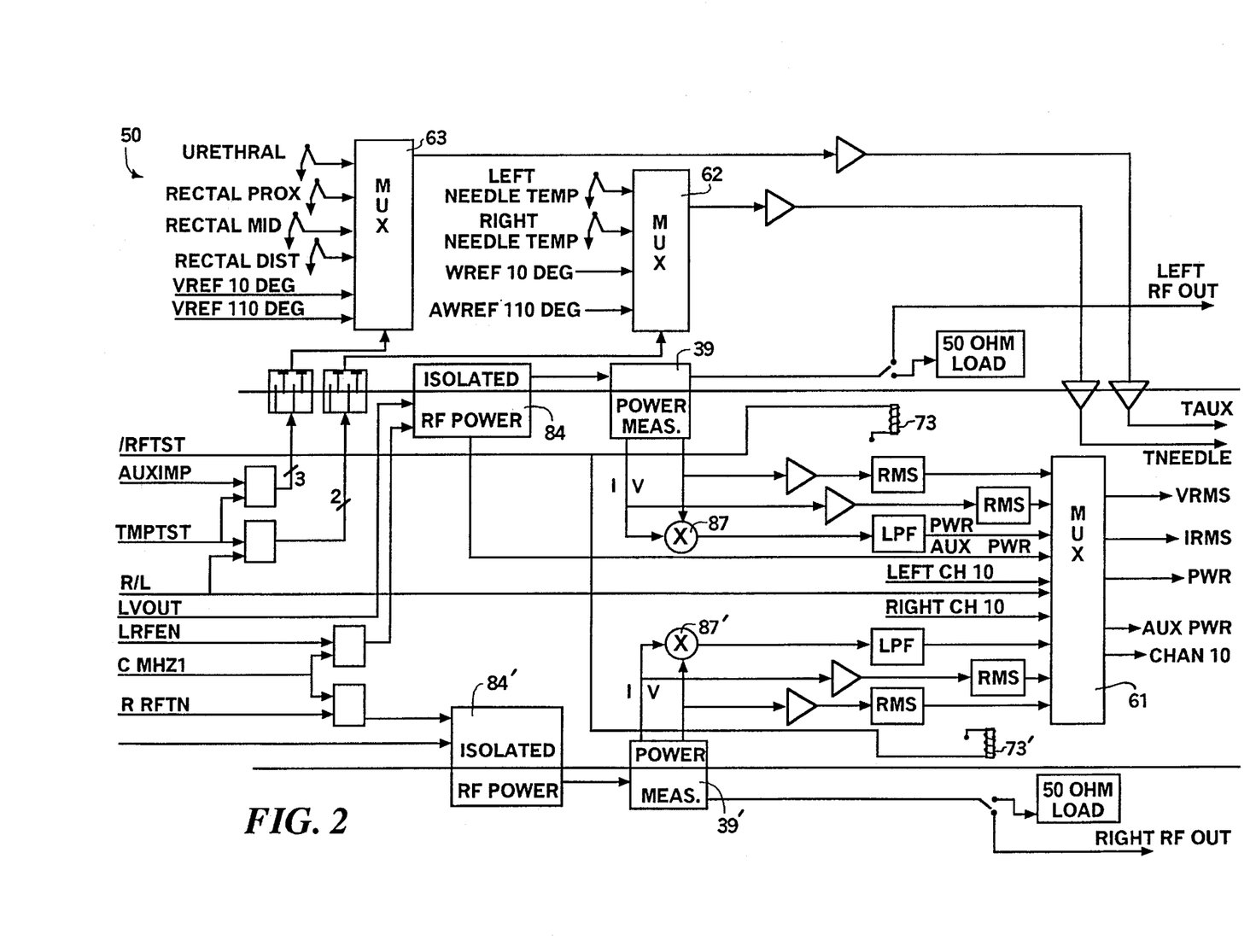
FIG. 2 is a block diagram of the RF/temperature board of FIG. 1.

The RF/temperature board of FIG. 1 is detailed in FIG. 2 with the RF board portion generating the variable output voltage RF signals used by the system to produce tissue heating. The RF outputs are generated by transformers whose center-tapped primary windings are driven by variable DC voltages. Isolated RF power 84 corresponds to the combination of converters 31 and 35 and transformer 36 of FIG. 1 with RF power 84' corresponding to the left RF channel of FIG. 1. Items 73 and 73' represent the internal load resistors connected to the RF outputs by the CPU board 20. The two primary windings of the transformers are alternately switched to generate square wave output RF signals which are filtered to provide sinusoidal output signals. The output voltage and current are monitored with sense transformers connected in parallel and in series with the tissue load. The sinusoidal voltage and current are combined in a four-quadrant multiplier on the board to form an analog power output signal with the voltage and current signals being separately converted into RMS analog outputs with an RMS-DC converter device to allow software verification of the power output signal. Additionally, voltage and current generated by DC supplies for each channel are measured and multiplied in analog multipliers 87, 87' to generate auxiliary power signals which can be read by software as an additional check on the output power delivered. RF probes which are connected to a patient are electrically isolated from the power supply.

The amount of tissue heating is monitored through thermocouples embedded in the RF probe and in a separate rectal probe. The thermocouple signals are multiplexed and conditioned into two thermalcouple outputs. Cold junction compensation on a thermocouple board containing the multiplexers 62 and 63 corrects thermocouple signals for changes in the internal temperature of the system. The thermocouple output signals are the needle temperatures of the right and left needle and the auxiliary temperatures from the urethral thermocouple on the RF probe tip and the three thermocouples on the rectal probe. These signals are amplified, then passed through optical isolators to maintain patient isolation. Each of the thermocouple board's multiplexers also may select either of two precision, stable low level reference voltages. By regularly checking these precise voltages the software can apply gain and offset correction to account for any residual gain or offset errors anywhere in the signal chain between the thermocouples and the A/D on the CPU.

The internal load resistors 73 and 73' are switched into the circuit during self test during a power-up sequence.

Thermal measurements for the system are sensed by thermocouples located near the needles on the catheter (left and right needle temperature), at the catheter tip (urethral temperature), and at three points in the rectal probe. The location of the thermocouples and the catheter is described in copending application Ser. No. 08/012,370. The small thermocouple potentials of approximately 40 microvolts per degree C are conditioned on the thermal measurement board which is mounted directly to the main RF board.

Figure 3:
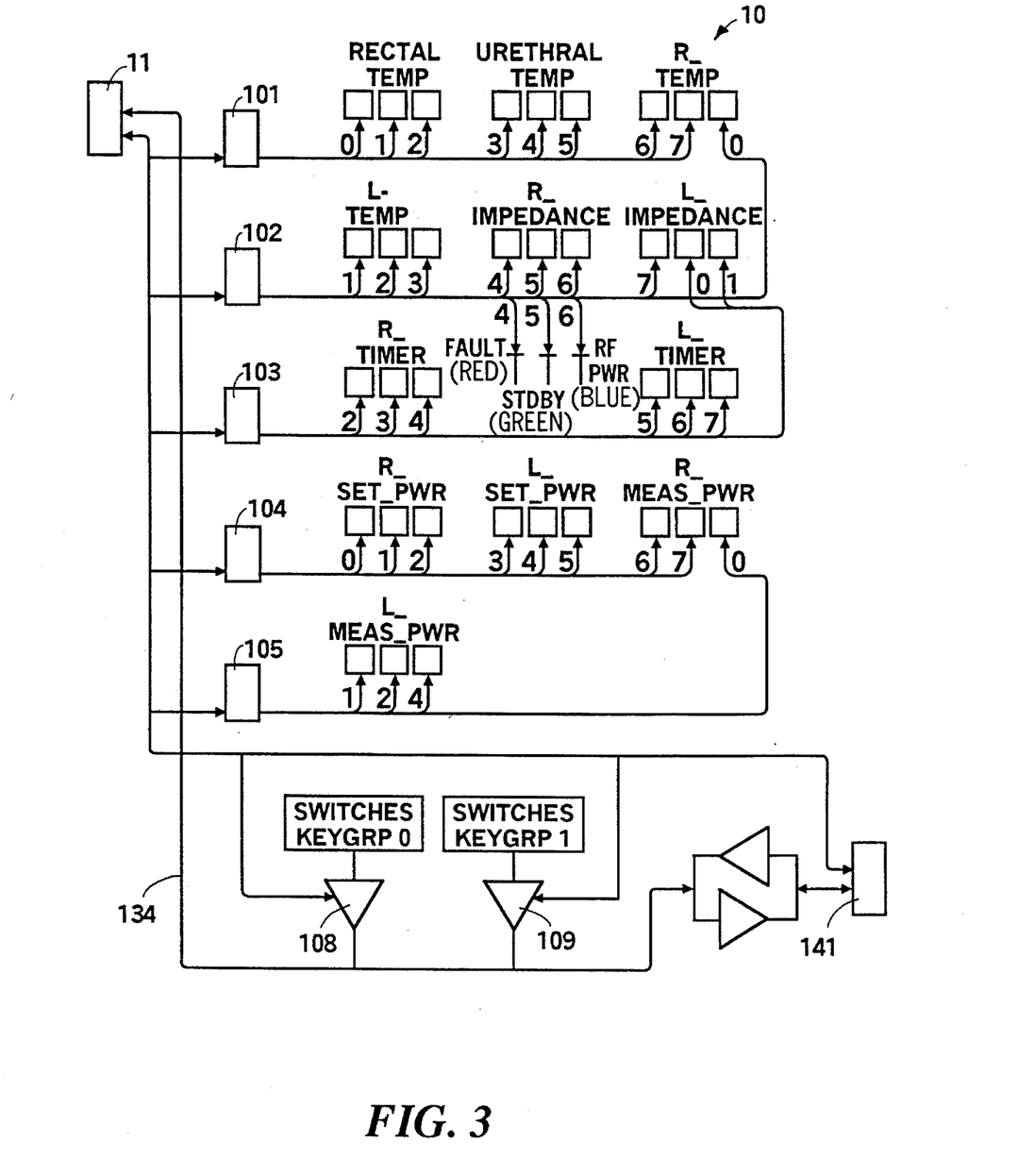
FIG. 3 is a block diagram of a front panel for the power delivery system of FIG. 1.

FIG. 3 illustrates the details of the connection of the front panel block 10 to the CPU 20 by means of connector 11. The front panel holds the digital and indicator lamp LED displays, an LCD panel interface and the function control switches. The LED displays shown in FIG. 3 are driven by an array of ICM 7228 devices 101–105 which each controls eight separate 8-segment LED digital displays. These devices 101–105 multiplex the digits by turning each digit on for one-eighth of the time at a 400 Hz rate. As a result the digits appear almost as bright as if they were on 100% of the time but the current required is dramatically reduced. FIG. 3 illustrates an association of three separate eight-segment LED digital displays for each of the temperature measurements, the impedance measurement, the timer settings and the power settings and the power measurement settings associated with the right and left channels respectively. Front panel switches pull down the switch voltage through resistors when the switches are depressed. Switch signals are buffered and gated by devices 108 and 109 onto the front panel data bus 134 when KEYGrP0 Or KEYGRP1 signals are activated. The LCD panel is driven by electronics 141 attached to the LCD module.

The RF dual channel generator of the present invention is capable of supplying up to 15 watts of RF energy to two needle electrodes on a catheter of the type described in copending application Ser. No. 08/012,370 over a range of tissue impedances from 50 to 500 ohms. The output power is controlled at the user selected level for a preset duration of up to 10 minutes. It monitors three temperatures measured by thermocouples in the catheter and three temperatures from thermocouples in a rectal probe. The front panel displays include seven segment numeric LED displays for power, impedance, elapsed time and temperature measurements in a 2 line by 40 character LCD display for text and messages. Front panel controls include power and duration settings and an on-off switch. The system includes a pneumatic foot switch and host RS 232 port for factory tests and calibration functions accessed via a host computer.

The processor control generator generates 462 kHz quasi-sinusoidal RF energy. The desired power and duration for each needle electrode is set by front panel controls and during operation, the actual measured power, tissue impedance and elapsed time are displayed on the front panel LED indicators. Six thermocouple temperature measurements are made in both READY and ON modes of operation. Automatic shut-off of RF power occurs when the preset duration is reached, or when the measured temperature exceeds predefined limits.

There are four operating states for the system for controlling power generation. There is a STAND-BY state, A ready state, An RF ON state and a DONE state. When the system is first turned on, it enters the STAND-BY state. When the front panel switch is pressed, it enters the READY state, and when the RF power is turned on, the system enters the RF ON state. When RF power shuts off, the system will enter the DONE state and then transition automatically to the READY state.

Figure 4:
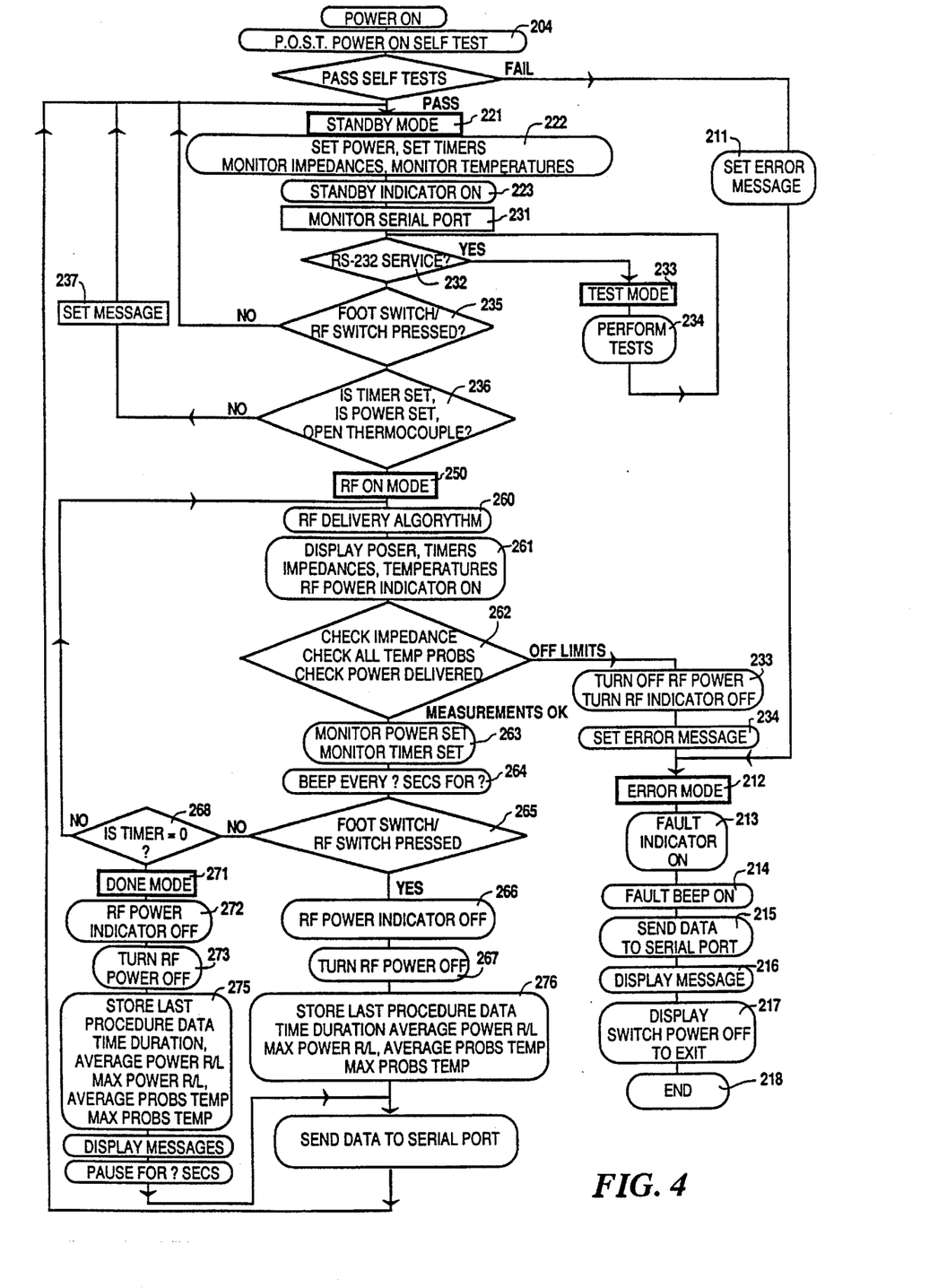
FIG. 4 is a flow chart for the operation of the RF delivery system according to the present invention.

When AC line power is turned on, a self-test is performed as shown in FIG. 3 at step 204. The tests performed are a CPU test, RAM write/read test, ROM CRC test, RF power generation and measurement test and temperature measurement subsystem test. During the self-test, the LED displays and indicators will all be lit and the piezo beeper will sound and the LCD display will indicate that a self-test is being performed. When the self-test is successfully passed, the software enters the STAND-BY state or mode. If the test is not passed an error message is set either indicating a CPU, RAM, a ROM or a RFG subsystem error. This branch is shown in FIG. 4 at steps 211 through 218.

After a successful self-test, the system enters the STAND-BY state with the left and right needle power set points set to 0 watts and the left and right needle durations set to 0.00 minutes. The temperature measurement subsystem is not active. When the front panel switch is pressed, the system will enter the READY state. The left and right RF outputs will be periodically activated at a low level so impedance measurements can be made. The system monitors the left and right set POWER-UP/DOWN, TIMER UP/DOWN, RF POWER and FOOT switches. When the UP/DOWN power switch is pressed the set power is incremented or decremented by 0.1 watt and the displays are updated. The power range is limited between 0 and 15 watts. When the left or right POWER-UP/DOWN switch is held, the left or right set power is automatically incremented with a power range of between 0 and 15 watts. Pressing the UP/DOWN TIMER switches provides an increment or a decrement of 1 second with the timer range between 0.00 and 9.59 minutes. Holding down of the timer switches provides an automatic increment to the set time in the same time range as the pressing of the switches. In other words one push of a switch will cause a 1 second increment in the timer switch while the continuous holding down of the switch will provide automatic incrementation up to 10 minutes or down to 0 minutes.

Pressing the footswitch provides a transition to the ON state. These settings are shown in FIG. 4 and covered by the step 221 to 223 and the steps 231 to 237 with the steps 232 to 234 indicating whether the RS 232 is active and in service for testing by a host computer.

The host computer will then direct the tests in step 234.

During the READY mode, temperature measurement is active on all six thermocouples with the left and right needle temperatures being read ten times per second and a filtered average being displayed on the LED displays of FIG. 3 at an update rate of once per second. The urethral temperature and the three rectal temperatures are read ten times per second and a filtered average is displayed on the LED display at an update rate of once per second. The maximum of the three rectal temperatures is displayed. These temperature measurements are obtained by performing A/D conversion on the appropriate analog channel and converting the resulting digital voltage reading to degrees C.

Also during the READY state, impedance is measured by intermittently applying a low level RF output voltage to each needle and measuring the resulting voltage and current, which are divided to measure impedance. This function is performed once each second. Voltage and current measurements are obtained by performing the A/D conversion on the appropriate analog channels and converting the resulting digital voltage reading to volts and amps of the RF signal.

Figure 5:
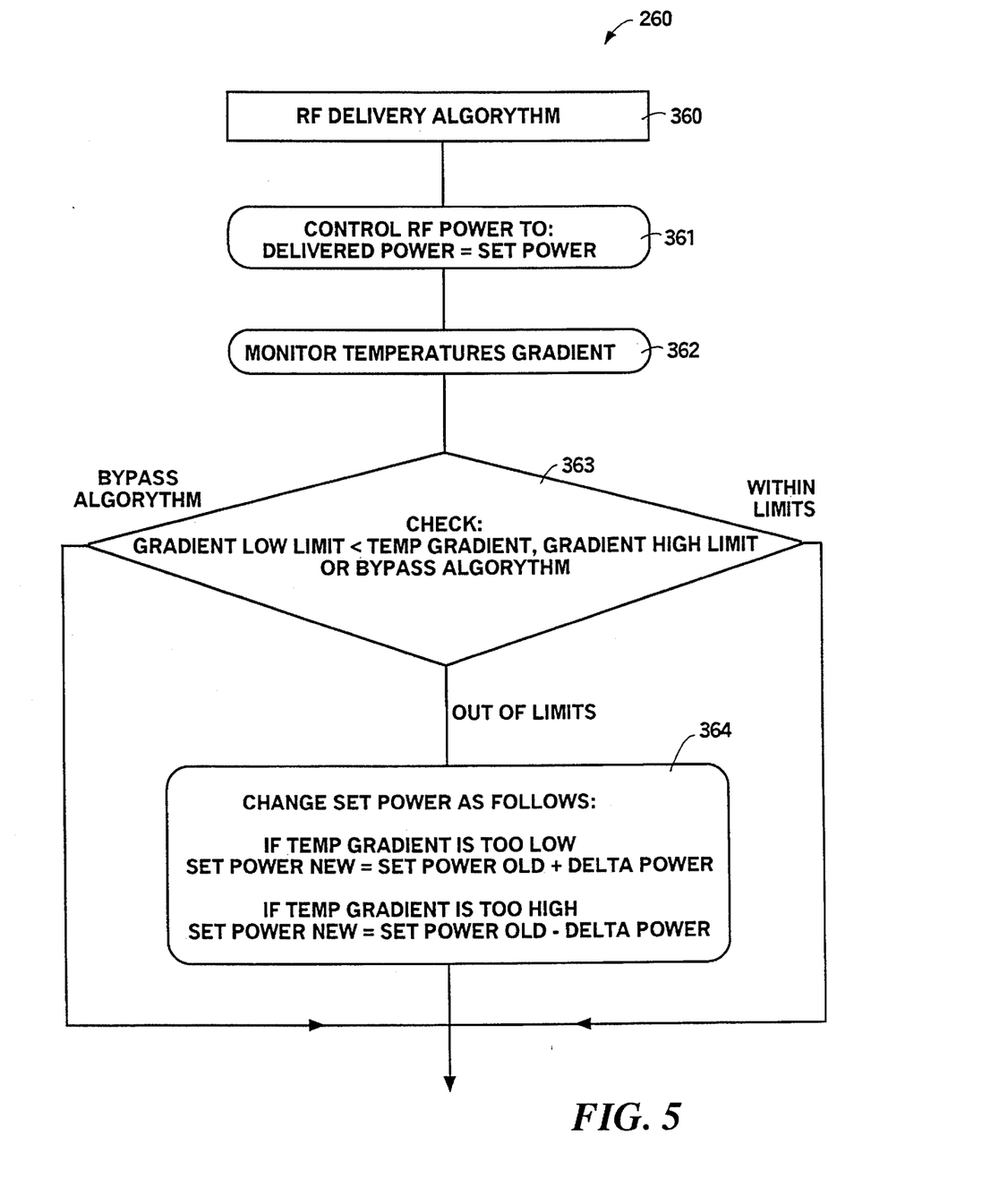
FIG. 5 is a flow chart of the RF delivery algorithm of FIG. 4.

When the system transitions into the RF ON mode 250, the RF power is generated and measurement, control, display and timer functions are active. The system enters the RF ON state when the foot switch is depressed. When the ON state begins, a control algorithm 260 which is shown in FIG. 4 and detailed in FIG. 5 is executed. The RF control power for each needle is delivered and increased toward the power set points. The measurement and display functions for power and impedance begin at 50 Hz in order to obtain instantaneous values of RMS RF voltage, RMS RF current and RF power. Impedance is computed from the ratio of RMS voltage to RMS current. Measured power and impedance are displayed on the numeric displays and updated every 0.5 seconds. The piezo beeper will sound every four seconds during the ON mode and will stop when the DONE mode is entered. If a fault occurs, the fault LED will be ON continuously and the piezo beeper will sound continuously. The system monitors the left and right set POWER-UP/DOWN, TIMER-UP/DOWN, RF power and foot switches. These actions are reflected by step 261 to 265 of FIG. 4.

In the ON state power is delivered to the left and right needles according to the user selected set power output and power duration. The ON state is entered from the READY state when the foot switch is depressed. The system leaves the RF POWER-ON state when the STANDBY switch is depressed or when the foot switch is depressed. The ON state is also automatically terminated when the preset time durations for both needles have been reached or if the measured temperature exceeds predefined limits. When the system leaves the ON state it enters the DONE state. These options are covered by steps 270, 266–268. During the ON mode, temperature measurement and display as well as selection of output power is the same as in the previously described READY state. As indicated previously, impedance during the ON state is measured by measuring the voltage and currents for each needle at 50 Hz and dividing the voltage and current to calculate the impedance and display it once per second. The measurement of RF power is accomplished during the ON state by performing an analog to digital conversion of the analog signal representing RF power at 50 Hz. This digital voltage is converted to power in watts for control and display purposes. RF power delivered during the ON state to each needle is controlled to maintain the power output set point with the RF generators for each of the left and right generator being controlled by a DAC control voltage. Any changes to the control voltage are determined by a digital proportional-integral control algorithm as shown in more detail in FIG. 5 by steps 360 to 364. The particulars of the delivery algorithm are the control of the RF power set that the delivered power is equal to the set power in step 361 and the temperature gradient is monitored in step 362. When the temperature gradient is greater than a lower limit and less than a high limit the power is continued and step 261 of FIG. 4 is entered. On the other hand if the temperature gradient is not within the limits the power setting is changed so that the power setting is incremented if the temperature gradient is too low and decremented if the temperature gradient is too high as shown in step 364. Step 363 also contains an alternative to the monitoring of the temperature gradient which involves bypassing the algorithm. Once the DONE mode is entered RF power generation is stopped. This can occur when the foot switch is depressed as indicated by steps 266 and 267 or when the timer reaches 0 minutes as indicated by steps 268 and 271–273. After updating termination status on the LCD screen as indicated by step 275 and 276 the system enters the READY mode.

As indicated previously, the test mode 233 and 234 can only be entered by command over the RS 232 interface and is used for testing the RF power generator during system calibration and final test. In this particular mode, only the RS 232 interface is active and the watchdog timer is toggled so that reading and writing through the system RAM and I/O ports will allow direct computer control of the system.

With the apparatus of FIG. 1 of the present invention acting in conjunction with the operating system by way of the CPU board 20, two separate RF generators can be used to control the right needle and the left needle to perform ablation in a number of various modes. Utilizing this system does not require symmetry either on the part of the physiology of the patient or the length of deployment of the needle. Both needles can be operated at essentially the same power and the same temperature or could selectively operate at different powers as it allows for automatic compensation for differences in deployment length of the needles or deployment length of the shields.

Furthermore, with the present invention it is possible to perform a plurality of self-tests when the unit is powered up so that each of the RF generators is connected to an internal test load so each channel can be tested thereby eliminating the need for calibration of temperature measurement circuits. A precision reference voltage source is incorporated as an input which can be switched into the circuitry. Thus, for example, there is a reference voltage source having a number of microvolts corresponding to for example 30° C. and there is a second reference voltage source corresponding to approximately 90° C. These accurate precision reference voltages will not change. The operating system reads these reference voltages and uses the values to convert the thermocouple voltages into temperature measurements without requiring an offset or scale factor adjustment. This is implemented through a multiplexing scheme wherein each of the thermocouples can be switched through a multiplexer into the amplifier stage and into the microcomputer as is seen in the FIG. 1 with the term ref-low and ref-high for each of the multiplexers 62 and 63. This provides two separate advantages. The first advantage is there is no need for calibrating the gain and offset because the computer provides this by reading the reference voltages. It is also possible to tell if the circuitry is working from the reference voltages through the amplifiers and back to the microcomputer because, if it is not working, the reference voltages will not be read as being the correct voltages. Thus it is a self-test as well as an autocalibration with respect to the thermocouple circuitry.

The reference voltages allow for a recomputation based on scale factors which accommodates the drifts in components and essentially calibrates these components so autocalibration occurs during operation.

Another significant advantage of the present invention is the use of multiplexers allows temperature information to be obtained across the patient isolation barrier. This avoids the connection of regular circuitry in a microcomputer directly to a thermocouple wire going into the patient. It is always required to have an isolation stage between signals going into a patient and a microcomputer. A transformer coupled or optically coupled isolation amplifier is normally used and by switching thermocouples several or all of the signals are sequential sent through the same isolation amplifier. This arrangement avoids having to require separate optically coupled isolation amplifiers for each thermocouple and furthermore only requires the testing of one signal path.

The algorithm for power delivery as detailed with respect to FIGS. 4 and 5 is a PID (proportional integral derivative) control algorithm which adjusts the output voltage of each channel individually to maintain a certain power. If the tissue impedance goes up, the system automatically increases the output voltage to maintain the same power. In the refinement discussed and shown in FIG. 5 output power is controlled as a function of the temperature change or rate being measured. That is, if the temperature is not increasing, the output power could be increased to maintain a certain temperature gradient. This temperature feedback control maintains a certain range of temperature gradients and increases the temperature to a therapeutic level without a doctor having to get involved and make that judgement.

Other possible areas of algorithm control involve impedance control whereby high impedance situations are detected where the tissue dries out and chars around the needle and effectively shuts off the power before fully developed lesions are produced. This algorithm detects the increase in impedance and provides for a reduction of the output power. This would avoid an extremely high impedance where the needle would essentially shut off and not deliver power to the tissue. It effectively monitors the rate of impedance change so that the rise in impedance will be matched by a reduction in the output power.

Figure 6:
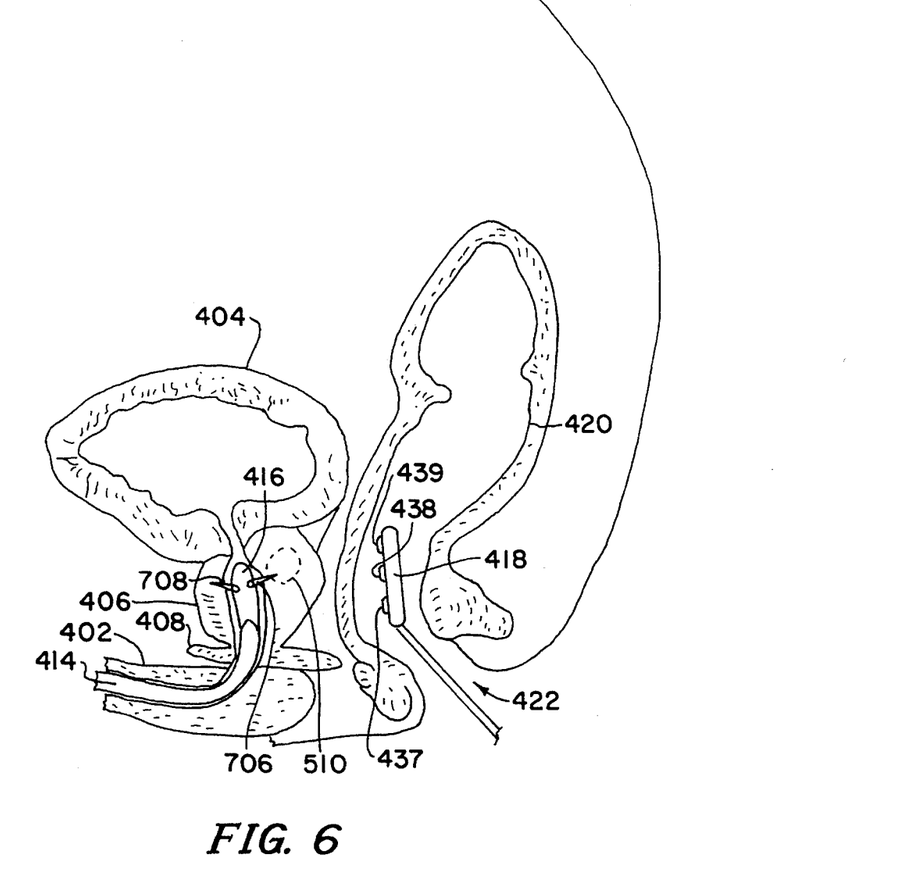
FIG. 6 is a cross-sectional drawing of the lower male anatomy showing the placement of a catheter and a prostate probe with the catheter dual channel power delivery system according to the preferred embodiment of the present invention.

FIG. 6 is a schematic cross-sectional drawing of the lower male anatomy during the use of a typical device for applying the controlled energy to the treated tissue according to the method and apparatus of the present invention. The urethra 402 extends from the urinary bladder 404 through the prostate 406 and with urogenital diaphragm 408. BPH is a condition characterized by constriction of the portion of the prosthetic urethra caused primarily by proliferation of benign glandular and stroma cells in the prostate. These nodules press the wall of the urethra inwardly, restricting the urethral diameter, and may at times press normal tissue outwardly possibly enlarging the prostate. Traditional treatments, short of removal of the prostate, have included either removal of tissue from the urethra to enlarge its lumen by resection or laser tissue destruction, or by expansion and heating of the tissues surrounding the urethra to a temperature which causes cell damage. The latter method is intended to reduce the swelling or enlargement of the prostate, and restore the urinary passage to at least a portion of its former diameter.

A catheter 414 with a stylet guide 416 is passed through the urethra to a position adjacent the prostate. The position of the guide 416 is precisely controlled, using an ultrasound image, for example, obtained from signals received from a conventional ultrasonic transducer 48 inserted through the anal opening 422 into the rectum 420 adjacent to the prostate. The guide facilitates easy positioning of the stylets into a precise location under ultrasonic imaging. The transducer 418 may also contain sensors 437, 438 and 439 for sensing, within the bowel region, any effects from heating tissue as will be described later. Optionally, the sensors 437, 438 and 439 can be a part of a separate instrument placed into the rectal area after removal of an ultrasonic probe and after the catheter 414 and stylet guide 416 have been positioned. FIG. 6 illustrates two stylets 706 and 708 with the stylet 706 having its end penetrated into a tissue area 570 which represents tissue to be ablated.

Figure 7:
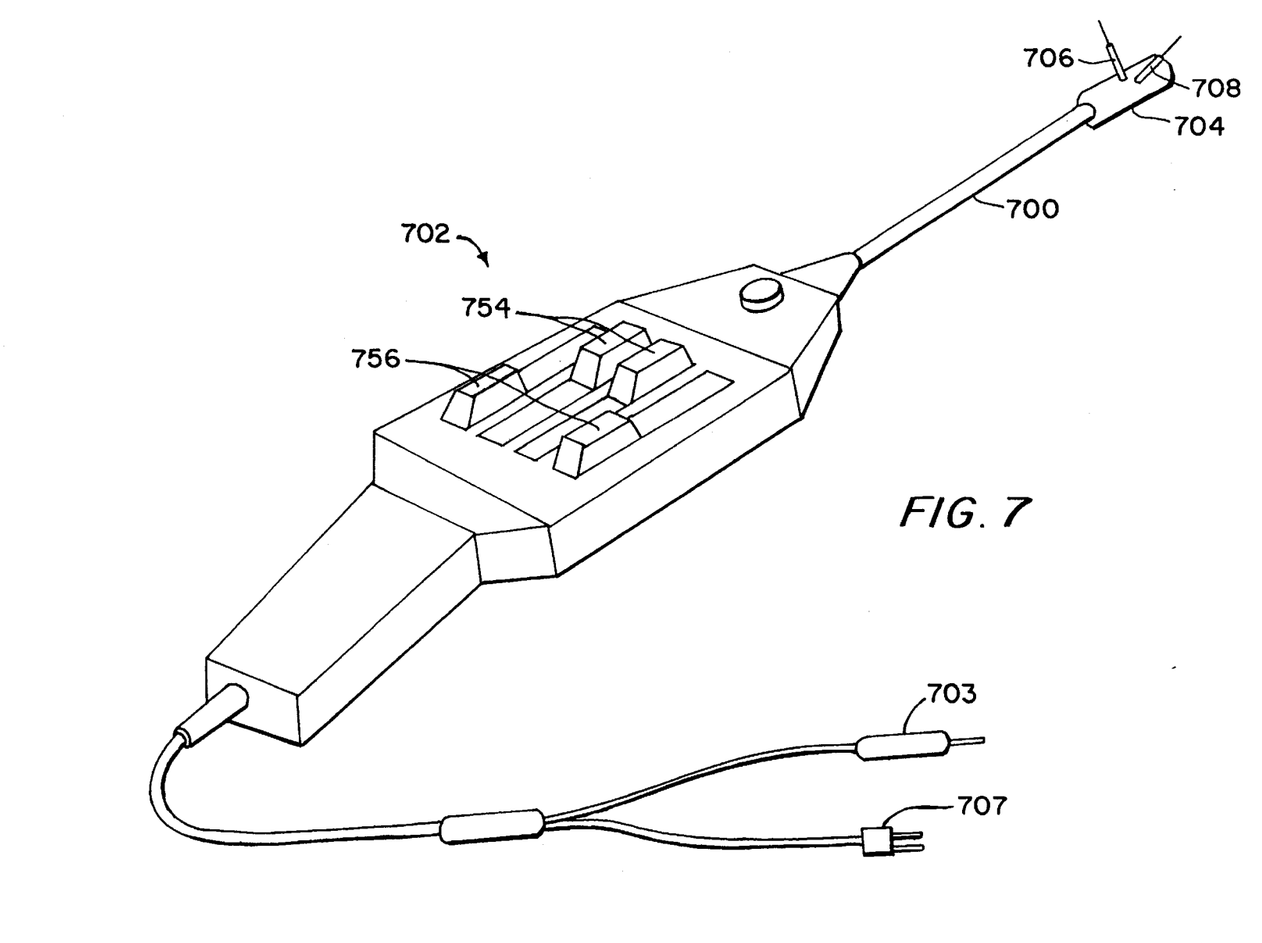
FIG. 7 is a top view of a two stylet embodiment of an RF ablation catheter utilizing the power application of the present invention.

FIG. 7 is a top view of a two stylet embodiment of an ablation catheter of FIG. 6 used to deliver power from the preferred method and apparatus of the present invention. The flexible catheter 700, attached to handle 702, has a terminal stylet guide 704 with two stylets 706 and 708. The handle has stylet sleeve cap 756 and electrode cap 754. The handle is also connected to an RF power connector 703 to be discussed in detail hereinafter. Also shown is a thermocouple connector 707. The portions of the catheter 700 leading from the handle 702 to the stylet guide 704 can optionally have a graduated stiffness. For example, the catheter can be designed to be more stiff near the handle and more flexible near the tip or any other stiffness profile desired. The catheter can be constructed of an inner slotted stainless steel tube with an outer flexible sleeve such as is described in copending application Ser. No. 790,648 filed Aug. 11, 1991, the entire contents of which are incorporated herein by reference. It can also be made of a coiled or braided wire to which an outer sleeve is bonded. The stylet of FIG. 7 is described in the copending application Ser. No. 08/012,370 filed Feb. 2, 1993.

Figure 7A:
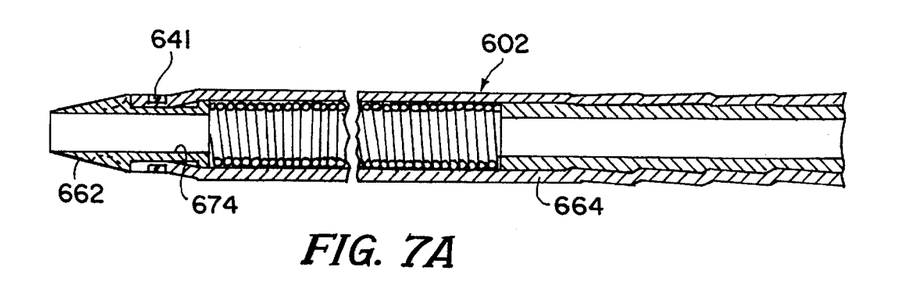
FIG. 7A is a side-view of a con-conductive sleeve covering each stylet of FIG. 7.

The stylet guide 416 has two stylets with sensors being respectively attached in the vicinity of each stylet 706,708. More particularly, the stylets of FIG. 7 each includes a non-conductive sleeve as illustrated in FIG. 7A. This non-conductive sleeve is discussed in detail in copending application Ser. No. 08/012,370. For purposes of the present application, the non-conductive sleeve has a tapered leading tip 662 and a rigid proximal portion 664. The center portion or the inner lumen 674 of the non-conductive sleeve 602 receives the stylet 706, 708. A temperature sensor 641 is mounted on the tip.

The system of FIG. 1 operates in conjunction with application of RF power in a unipolar mode. That is, it operates by providing a measurement of impedance between each needle and an indifferent electrode placed on the patient's back as is known and discussed in application Ser. No. 08/012,370. However, the design of the power supply of FIG. 1 is such that the right and left channel needle outputs can be operated in several different modes. With the operation in unipolar mode having the indifferent electrode attached to the patient, the channels are provided with "in phase" power. That is, each of the needles produces a sinusoid type waveform output and if these two waveforms were examined they would essentially overlap in phase with each other. Therefore, the two needles are at the same voltage level at all times and there is no current flow between the two needles because current flows from high voltage to low voltage. Thus, in the case where the needles are at the same voltage and the indifferent electrode on the patient's skin is at a 0 voltage reference point, the current flows from the needles to the tissue to the indifferent electrode. However, by changing a programmable bit in the control hardware, the phasing of the left and right channel outputs can be such that they are not in phase but that they are out of phase. This would mean that when a waveform through one channel is at a maximum positive, it would be at a maximum negative in the other channel. This is a 180 degree phase difference and in that situation the current would naturally want to flow from one needle to the other needle to set up a bipolar effect.

The major difference in ablation due to the dual power supply of the present invention can be appreciated from a comparison of a single power supply for both needles or channels with the dual power supply disclosed herein.

When two needles are driven by a single power supply, a circuit diagram for the completed circuit would be similar to a needle going through tissue to the indifferent electrode which would look schematically as a resistor. Therefore, each needle would have essentially a resistor attached to it and because both needles are being driven at the same time there are two resistances in parallel with each other being driven by a voltage source that is controllable.

However, with a single voltage source, all that is able to be controlled is the voltage across these two parallel resistance paths and this resistance is the tissue resistance which and is highly likely to be a function of the contact with the tissue. Furthermore each one of the needles may be different and there is no way of controlling what happens with one needle or the other, As a result, what is most likely to occur is that the path which has the lower resistance will preferentially obtain more of the current.

Thus it is highly likely that any kind of ablation by the needle which has the higher resistance almost invariably forces a lot more energy into the path that has the lower resistance which will heat that particular path and cause it to go to a higher impedance condition. Thus there is a likelihood of different lesions around different needles in a dual stylet system having but a single power source. The result of this excessive lesion or excessive energy might be a burning of the prostate completely or the creation of heat that could hurt a nearby organ such as the bowel. Obviously, this would not occur because of the temperature feedback but it would cause a premature termination without a second lesion being satisfactorily obtained.

With the dual channel system disclosed herein, the circuit model provides two individual voltage sources driving two individual resistances which can be controlled separately to deliver precise amounts of power. It also incorporates temperature feedback so there is an increase in control and a drastically increased likelihood of a much more uniform generation of lesions around both needles. Because the needles are deployed relatively close to one another, and because of the dual channel of the present invention, uniform lesions will be obtained around each needle. This will tend to fill in the space between the two needles in order to obtain a precise large uniform lesion as opposed to having a single lesion around one needle and almost nothing around the second needle when a single channel is used.

Obviously, numerous and additional modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A dual channel RF power delivery and monitoring system for delivering controlled radio energy to each of two stylets adjustably protruding from a catheter in order to provide for destruction of target tissue in the area of each of said stylets, said system comprising:

two independent power delivery channels wherein each of said channels includes a means for controlling power output from said channels;

temperature measurement means responsive to input temperature signals associated with said catheter and said stylets;

autocalibration means including a precision reference voltage source switchably connected to said temperature measurement means;

multiplexing means for switchably receiving said input temperature signals and for switching said reference voltage source.

2. The dual channel system of claim 1, wherein said temperature input signals are provided by sensors associated with each of said stylets and said catheter.

3. The dual channel system of claim 1, further including a first means for monitoring the impedance of a first circuit completed by one of said channels, one of said stylers and a human body containing said target tissue in the vicinity of said one stylet and a second means for monitoring the impedance of a second circuit completed by the other one of said channels, the other one of said stylets and said human body containing said target tissue in the vicinity of the other stylet.

4. A method of independently delivering power and monitoring the condition of two separate stylets in a catheter, comprising the steps of:

providing a first controlled radio frequency energy to one of said stylets at a radio frequency selected from a range which does not electrically excite human nervous system tissue;

providing a second controlled radio frequency energy to the other one of said stylets at a radio frequency selected from a range which does not electrically excite human nervous system tissue, wherein said second controlled radio frequency energy is independent of said first radio frequency energy;

monitoring the temperature of target tissue proximal to each of said stylets during the respective providing of said first and second radio frequency energies;

maintaining said first and second radio frequency energies at respective energy levels and for respective durations to ablate said target tissue proximal to each of said stylets;

cutting off said providing of first radio frequency energy when the monitored temperature of said first styler target tissue exceeds a first predetermined value; and cutting off said providing of second radio frequency energy when the monitored temperature of said second stylet target tissue exceeds a second predetermined value.

5. The method according to claim 4, wherein said steps of maintaining said first and second controlled radio frequency energies include maintaining said first and second energies at a substantially constant operator selectable energy.

6. The method according to claim 4, wherein said target tissue is located in a prostate of a human male and wherein said catheter is positioned in the urethra of said male.

7. The method according to claim 4, wherein the step of monitoring the temperature of said target tissue includes the step of providing a sensor in proximity to each of said stylets.

8. The method according to claim 4, further including the step of monitoring at least one temperature of body organs in the vicinity of said target tissue and automatically stopping delivery of energy to both of said stylets when said temperature of said monitored adjacent organ temperature exceeds a predetermined safe organ temperature.

9. The method according to claim 4, and further including the step of controllably operating said first radiofrequency energy either in phase or out of phase with said second radiofrequency energy.

* * * * *